United States Patent
Choo et al.

(10) Patent No.: US 10,435,408 B2
(45) Date of Patent: Oct. 8, 2019

(54) AZEPINE DERIVATIVES AS 5-HT$_7$ RECEPTOR MODULATORS

(71) Applicant: KOREA INSTITUTE OF SCIENCE AND TECHNOLOGY, Seoul (KR)

(72) Inventors: Hyunah Choo, Seoul (KR); Youngjae Kim, Seoul (KR); Jihye Seong, Seoul (KR); Ghil Soo Nam, Seoul (KR); Yong Seo Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/738,225

(22) PCT Filed: Nov. 6, 2017

(86) PCT No.: PCT/KR2017/012493
§ 371 (c)(1),
(2) Date: Dec. 20, 2017

(87) PCT Pub. No.: WO2018/117406
PCT Pub. Date: Jun. 28, 2018

(65) Prior Publication Data
US 2018/0312509 A1 Nov. 1, 2018

(30) Foreign Application Priority Data
Dec. 22, 2016 (KR) .......................... 10-2016-0176681

(51) Int. Cl.
| | | |
|---|---|---|
| C07D 487/04 | (2006.01) | |
| C07D 498/04 | (2006.01) | |
| A61K 31/55 | (2006.01) | |
| A61K 31/4162 | (2006.01) | |
| A61P 25/22 | (2006.01) | |
| A61P 25/24 | (2006.01) | |

(52) U.S. Cl.
CPC ........ *C07D 487/04* (2013.01); *A61K 31/4162* (2013.01); *A61K 31/55* (2013.01); *A61P 25/22* (2018.01); *A61P 25/24* (2018.01); *C07D 498/04* (2013.01); *Y02P 20/55* (2015.11)

(58) Field of Classification Search
CPC .... C07D 487/04; C07D 498/04; A61K 31/55; A61K 31/4162; A61P 25/22; A61P 25/24

USPC .................. 540/577; 514/211.1; 614/211.1
See application file for complete search history.

(56) References Cited

U.S. PATENT DOCUMENTS

| | | |
|---|---|---|
| 2006/0003990 A1 | 1/2006 | Bennani et al. |
| 2006/0111348 A1 | 5/2006 | Kampen et al. |
| 2012/0196848 A1 | 8/2012 | Matsumoto et al. |

FOREIGN PATENT DOCUMENTS

| | | |
|---|---|---|
| KR | 10-2007-0023633 A | 2/2007 |
| KR | 10-2009-0104924 A | 10/2009 |
| WO | WO 97/29097 | 8/1997 |
| WO | WO 97/48648 | 12/1997 |
| WO | WO 97/48681 | 12/1997 |
| WO | WO 97/49695 | 12/1997 |
| WO | WO 99/24022 | 5/1999 |
| WO | WO 00/00472 | 1/2000 |
| WO | WO 03/048118 | 6/2003 |
| WO | WO 2005/040169 A2 | 5/2005 |

OTHER PUBLICATIONS

Pccompound 1-8, Create Date Aug. 19, 2012 to Apr. 10, 2017.*
Jimmy T. Liang et al., "Convergent Synthesis of a 5HT$_7$/5HT$_2$ Dual Antagonist", Organic Process Research & Development, 2011, pp. 876-882, vol. 15.
STN Registry Database Results CAS Registry No. 1422141-67-0, Publication Date Mar. 1, 2013.

* cited by examiner

*Primary Examiner* — Venkataraman Balasubramanian
(74) *Attorney, Agent, or Firm* — Rabin & Berdo, P.C.

(57) ABSTRACT

Azepine derivatives acting on 5-HT$_7$ receptors and pharmaceutically acceptable salts thereof are disclosed. The azepine derivatives and the pharmaceutically acceptable salts thereof have high binding affinities for and high antagonistic activities on 5-HT$_7$ receptors. Due to these advantages, the azepine derivatives and the pharmaceutically acceptable salts thereof can be applied to therapeutic or prophylactic agents for central nervous system diseases, such as depression, migraine, anxiety, pain, inflammatory pain, neuropathic pain, body temperature dysregulation, biorhythm dysregulation, sleep disturbance, and smooth muscle diseases where 5-HT$_7$ receptors antagonistic activity is required.

7 Claims, No Drawings

AZEPINE DERIVATIVES AS 5-HT₇ RECEPTOR MODULATORS

BACKGROUND OF THE INVENTION

1. Field of the Invention

The present invention relates to azepine derivatives as 5-HT$_7$ receptor modulators, pharmaceutically acceptable salts thereof, methods for preparing these compounds, and pharmaceutical compositions including these compounds as active ingredients.

2. Description of the Related Art

Serotonin acts as a neurotransmitter on 14 different serotonin receptors that are widely distributed throughout the organs of the body and is responsible for various physiological phenomena. Serotonin receptors cause various physiological responses through interactions with serotonin. Among them, 5-HT$_7$ receptors, the most recently identified serotonin subtype receptors, are widely distributed, particularly in the hypothalamus, thalamus, hippocampus, and cortex and are known to play an important role in body temperature regulation, biorhythm regulation, learning, memory, sleep, and hippocampal neurotransmission. 5-HT$_7$ receptors are also known to be involved in diseases such as depression, migraine and anxiety and neurological disorders such as inflammatory pain and neuropathic pain.

Many efforts have been made to develop 5-HT$_7$ receptor antagonists and agonists but only a few selective 5-HT$_7$ receptor antagonists are currently known. For example, WO97/29097, WO03/048118, WO97/48648, WO97/48681, and WO97/49695 reported antagonists having a sulfonamide moiety as a basic skeleton. Further, WO99/24022 and WO00/00472 reported tetrahydroisoquinoline derivatives acting on 5-HT$_7$ receptors.

Despite the considerable research efforts, there is still a need to find 5-HT$_7$ receptor modulators that are selective for 5-HT$_7$ receptors, have good pharmacokinetic profiles, and are effective against diseases associated with body temperature regulation, biorhythms regulation, sleep, and smooth muscles as well as the above-described diseases.

SUMMARY OF THE INVENTION

It is a first object of the present invention to provide azepine derivatives acting on 5-HT$_7$ receptors and pharmaceutically acceptable salts thereof.

It is a second object of the present invention to provide methods for preparing the azepine derivatives.

It is a third object of the present invention to provide pharmaceutical compositions including the azepine derivatives or pharmaceutically acceptable salts thereof as active ingredients that have pharmaceutical activity against depression, migraine, anxiety, pain, inflammatory pain, neuropathic pain, body temperature dysregulation, biorhythm dysregulation, sleep disturbance or smooth muscle diseases.

One aspect of the present invention provides the azepine derivatives represented by Formula 1:

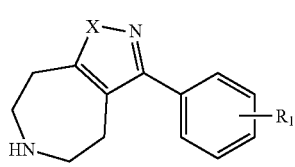

(1)

wherein X is NH or O and R$_1$ is selected from hydrogen, halogen, C$_1$-C$_6$ alkyl, C$_1$-C$_6$ alkoxy, halogenated C$_1$-C$_6$ alkyl, and hydroxyl, or a pharmaceutically acceptable salts thereof.

A further aspect of the present invention provides a method for preparing the azepine derivatives represented by Formula 1, including subjecting a compound of Formula 2:

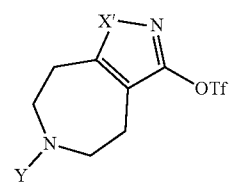

(2)

wherein X' is NR$_2$ or O, R$_2$ is —C(O)OC(CH$_3$)$_3$, Y is —C(O)OC(CH$_3$)$_3$ or —C(O)OCH$_2$CH$_3$ as an amine protecting group, and Tf is trifluoromethanesulfonyl, to the Suzuki coupling reaction with a compound of Formula 3:

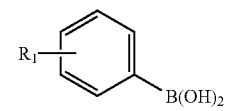

(3)

wherein R$_1$ is as defined in Formula 1, and removing the amine protecting group.

Another aspect of the present invention provides pharmaceutical compositions for preventing and treating central nervous system diseases, including the azepine derivatives represented by Formula 1 or pharmaceutically acceptable salts thereof as active ingredients.

Specifically, the central nervous system diseases may be selected from the group consisting of depression, migraine, anxiety, pain, inflammatory pain, neuropathic pain, body temperature dysregulation, biorhythm dysregulation, sleep disturbance, and smooth muscle diseases.

The azepine derivatives and the pharmaceutically acceptable salts thereof according to the present invention have high binding affinities for and high antagonistic activities on serotonin 5-HT$_7$ receptors. Therefore, the pharmaceutical compositions of the present invention are effective in treating and preventing central nervous system diseases, specifically, depression, migraine, anxiety, pain, inflammatory pain, neuropathic pain, body temperature dysregulation, biorhythm dysregulation, sleep disturbance, and smooth muscle diseases where 5-HT$_7$ antagonistic activity is required.

DETAILED DESCRIPTION OF THE INVENTION

The present invention will now be described in more detail.

According to one aspect of the present invention, there is provided the azepine derivatives represented by Formula 1:

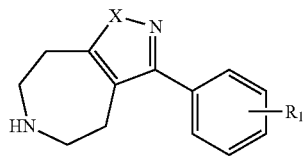

(1)

wherein X is NH or O and R₁ is selected from hydrogen, halogen, $C_1$-$C_6$ alkyl, $C_1$-$C_6$ alkoxy, halogenated $C_1$-$C_6$ alkyl, and hydroxyl.

The $C_1$-$C_6$ alkyl may be a straight-chain or branched alkyl group. Specifically, the $C_1$-$C_6$ alkyl may be selected from methyl, ethyl, propyl, isopropyl, butyl, isobutyl, t-butyl, hexyl, and isohexyl.

The $C_1$-$C_6$ alkoxy may be selected from methoxy, ethoxy, propoxy, butoxy, and pentoxy.

The halogenated $C_1$-$C_6$ alkyl may be a $C_1$-$C_6$ alkyl group substituted with one to three terminal halogen atoms and may be, for example, trifluoromethyl or trifluoroethyl but is not limited thereto.

The halogen may be selected from fluorine, chlorine, bromine, and iodine.

The azepine derivatives may be a hexahydropyrazolo azepine or a tetrahydroisoxazolo azepine.

The pharmaceutically acceptable salts are not particularly limited and may be any of those known in the art. Specific examples of such pharmaceutically acceptable salts include salts with non-toxic inorganic acids such as hydrochloric acid, hydrobromic acid, sulfonic acid, amidosulfuric acid, phosphoric acid, and nitric acid and salts with non-toxic organic acids such as acetic acid, propionic acid, succinic acid, glycolic acid, stearic acid, lactic acid, tartaric acid, citric acid, para-toluenesulfonic acid, and methanesulfonic acid.

Specifically, the azepine derivatives represented by Formula 1 may be, for example, selected from, but not limited to, the following compounds:

Compound 1: 3-Phenyl-1,4,5,6,7,8-hexahydropyrazolo[3,4-d]azepine;

Compound 2: 3-(2-Fluorophenyl)-1,4,5,6,7,8-hexahydropyrazolo[3,4-d]azepine;

Compound 3: 3-(3-Fluorophenyl)-1,4,5,6,7,8-hexahydropyrazolo[3,4-d]azepine;

Compound 4: 3-(2-Chlorophenyl)-1,4,5,6,7,8-hexahydropyrazolo[3,4-d]azepine;

Compound 5: 3-(3-Chlorophenyl)-1,4,5,6,7,8-hexahydropyrazolo[3,4-d]azepine;

Compound 6: 3-(4-Chlorophenyl)-1,4,5,6,7,8-hexahydropyrazolo[3,4-d]azepine;

Compound 7: 3-(o-tolyl)-1,4,5,6,7,8-hexahydropyrazolo[3,4-d]azepine;

Compound 8: 3-(m-tolyl)-1,4,5,6,7,8-hexahydropyrazolo[3,4-d]azepine;

Compound 9: 3-(p-tolyl)-1,4,5,6,7,8-hexahydropyrazolo[3,4-d]azepine;

Compound 10: 3-Phenyl-5,6,7,8-tetrahydro-4H-isoxazolo[4,5-d]azepine;

Compound 11: 3-(2-Fluorophenyl)-5,6,7,8-tetrahydro-4H-isoxazolo[4,5-d]azepine

Compound 12: 3-(3-fluorophenyl)-5,6,7,8-tetrahydro-4H-isoxazolo[4,5-d]azepine

Compound 13: 3-(4-Fluorophenyl)-5,6,7,8-tetrahydro-4H-isoxazolo[4,5-d]azepine

Compound 14: 3-(2-Chlorophenyl)-5,6,7,8-tetrahydro-4H-isoxazolo[4,5-d]azepine

Compound 15: 3-(3-Chlorophenyl)-5,6,7,8-tetrahydro-4H-isoxazolo[4,5-d]azepine

Compound 16: 3-(4-Chlorophenyl)-5,6,7,8-tetrahydro-4H-isoxazolo[4,5-d]azepine

Compound 17: 3-(o-tolyl)-5,6,7,8-tetrahydro-4H-isoxazolo[4,5-d]azepine

Compound 18: 3-(m-tolyl)-5,6,7,8-tetrahydro-4H-isoxazolo[4,5-d]azepine

Compound 19: 3-(p-tolyl)-5,6,7,8-tetrahydro-4H-isoxazolo[4,5-d]azepine

Compound 20: 3-(2-Methoxyphenyl)-5,6,7,8-tetrahydro-4H-isoxazolo[4,5-d]azepine.

The present invention also provides a method for preparing the azepine derivatives represented by Formula 1:

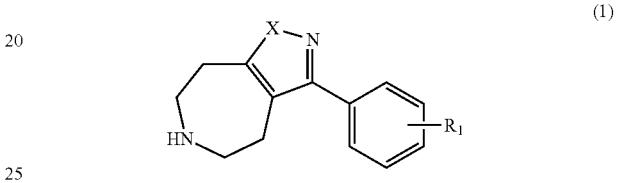

(1)

wherein X is NH or O and R₁ is selected from hydrogen, halogen, $C_1$-$C_6$ alkyl, $C_1$-$C_6$ alkoxy, halogenated $C_1$-$C_6$ alkyl, and hydroxyl.

Specifically, the method of the present invention includes subjecting a compound of Formula 2:

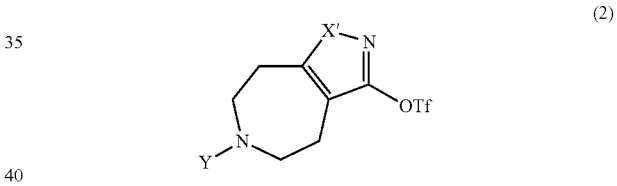

(2)

wherein X' is NR₂ or O, R₂ is —C(O)OC(CH₃)₃, Y is —C(O)OC(CH₃)₃ or —C(O)OCH₂CH₃ as an amine protecting group, and Tf is trifluoromethanesulfonyl, to the Suzuki coupling reaction with a compound of Formula 3:

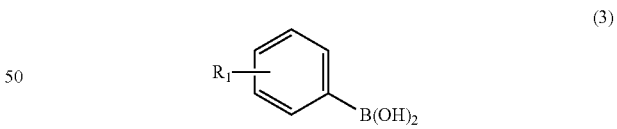

(3)

wherein R₁ is as defined in Formula 1, and removing the amine protecting group.

In Formula 2, Y is —C(O)OC(CH₃)₃ when X' is NR₂ and Y is —C(O)OCH₂CH₃ when X' is O.

The Suzuki coupling reaction of the compound of Formula 2 with the compound of Formula 3 may be carried out in an organic solvent in the presence of a palladium catalyst and a base. Specifically, this reaction may be allowed to proceed under reflux at 60 to 100° C. for 12 to 24 hours. Any general palladium catalyst for coupling reactions may be used without limitation. Preferably, the palladium catalyst is Pd(PPh₃)₄ or PdCl₂(dppf). The base may be, for example, K₃PO₄ and may be used in combination with a salt such as KBr during the reaction. The organic solvent may be selected from the group consisting of acetonitrile, dichloromethane, dichloroethane, tetrahydrofuran, $C_1$-$C_6$ alcohol, N,N-dimethylformamide, dimethyl sulfoxide, ethyl acetate, dioxane, and chloroform. The organic solvent is preferably tetrahydrofuran or 1,4-dioxane.

The $C_1$-$C_6$ alcohol may be selected from methanol, ethanol, propanol, butanol, and isopropanol.

The amine protecting group may be removed by acid treatment. Specifically, when Y is —C(O)OC(CH$_3$)$_3$, a dilute solution of hydrochloric acid in diethyl ether may be used to remove the amine protecting group. In this case, the hydrochloric acid is preferably present at a concentration of 0.8 to 1.5 N. When Y is —C(O)OCH$_2$CH$_3$, a dilute solution of hydrobromic acid in acetic acid may be used to remove the amine protecting group. In this case, the hydrobromic acid may be present in an amount of 30 to 40% by weight.

The azepine derivatives represented by Formula 1 may also be converted into a pharmaceutically acceptable salts thereof with a non-toxic inorganic acid such as hydrochloric acid, hydrobromic acid, sulfonic acid, amidosulfuric acid, phosphoric acid or nitric acid or a non-toxic organic acid such as acetic acid, propionic acid, succinic acid, glycolic acid, stearic acid, lactic acid, tartaric acid, citric acid, para-toluenesulfonic acid or methanesulfonic acid.

The compound of Formula 2 may be prepared by reacting a compound of Formula 4:

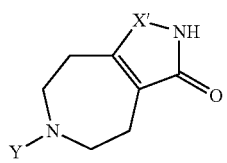

(4)

wherein X', $R_2$, and Y are as defined above, with Tf$_2$NPh.

In the reactant Tf$_2$NPh, Tf is trifluoromethanesulfonyl and Ph is phenyl.

According to one embodiment of the present invention, the compound of Formula 2 may be prepared by dissolving the compound of Formula 4 in an organic solvent, preferably dichloromethane, adding Tf$_2$NPh and DIPEA to the solution, and refluxing the mixture for 6 to 24 hours.

According to one embodiment of the present invention, the reaction mixture may be extracted with any suitable organic solvent known in the art. Specifically, the reaction mixture is extracted with an organic solvent selected from dichloromethane, diethyl ether, and ethyl acetate and water, and the organic layer is collected, dried to remove water molecules, concentrated, and purified by any suitable technique known in the art, preferably by column chromatography on silica gel to afford the desired compound represented by Formula 2.

On the other hand, the compound of Formula 4 may be prepared by a) reacting a compound of Formula 5:

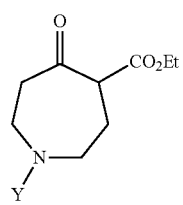

(5)

wherein Y is —C(O)OC(CH$_3$)$_3$ or —C(O)OCH$_2$CH$_3$ and Et is ethyl, with hydrazine and introducing $R_2$ into the compound of Formula 4.

Alternatively, the compound of Formula 4 may be prepared by b) reacting the compound of Formula 5 with ethylene glycol to protect the ketone group and reacting the reaction product with hydroxylamine. Y in Formula 5 is —C(O)OC(CH$_3$)$_3$ when the compound of Formula 4 is prepared by a) and is —C(O)OCH$_2$CH$_3$ when the compound of Formula 4 is prepared by b).

The compound represented by Formula 5 may be prepared by reacting a compound represented by Formula 6:

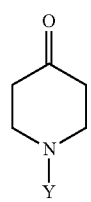

(6)

wherein Y is as defined above, with ethyl diazoacetate and BF$_3$OEt$_2$.

According to one embodiment of the present invention, the reaction may be carried out with stirring in an organic solvent at −40 to −10° C. for 20 to 120 minutes. The organic solvent is the same as that described above and is preferably diethyl ether. Specifically, the compound of Formula 6 is dissolved in diethyl ether, a solution of ethyl diazoacetate in diethyl ether at −40 to −10° C. and a solution of BF$_3$OEt$_2$ in diethyl ether at −40 to −10° C. are slowly added thereto, followed by stirring. At this time, the temperature of the reaction mixture is preferably maintained at −40 to −10° C. After the temperature is allowed to rise to room temperature, an aqueous solution of K$_2$CO$_3$ is added until nitrogen gas is no longer evolved. The reaction mixture may be purified by any suitable technique known in the art. In the Examples section that follows, the reaction mixture was purified by extraction and column chromatography to afford the desired compound.

According to a further aspect of the present invention, there are provided pharmaceutical compositions for preventing and treating central nervous system diseases, including the azepine derivatives represented by Formula 1 or pharmaceutically acceptable salts thereof as an active ingredient.

Particularly, the central nervous system diseases may be selected from the group consisting of depression, migraine, anxiety, pain, inflammatory pain, neuropathic pain, body temperature dysregulation, biorhythm dysregulation, sleep disturbance, and smooth muscle diseases.

According to the present invention, the azepine derivatives represented by Formula 1 or pharmaceutically acceptable salt thereof has high binding affinity for 5-HT$_7$ receptors and exerts selective antagonistic or agonistic activity on 5-HT$_7$ receptors. Therefore, the pharmaceutical compositions of the present invention are effective in treating and preventing central nervous system diseases where antagonistic or agonistic activity on 5-HT$_7$ receptors is required.

According to one embodiment of the present invention, the azepine derivatives or pharmaceutically acceptable salts thereof may be formulated with carriers, adjuvants or diluents to produce forms suitable for oral or parenteral administration by suitable methods known in the art.

Examples of the carriers, adjuvants or diluents include lactose, dextrose, sucrose, sorbitol, mannitol, xylitol, erythritol, maltitol, starch, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

The formulations may further include one or more additives, such as fillers, extenders, binders, wetting agents, disintegrants, and surfactants. Lubricants, such as magnesium stearate and talc, may be further added during the formulation.

For oral administration, the azepine derivatives or pharmaceutically acceptable salts thereof may be formulated into tablets, capsules, solutions, syrups, and suspensions. For parenteral administration, the azepine derivatives or pharmaceutically acceptable salts thereof may be formulated into injectables for intraperitoneal, subcutaneous, intramuscular, and transdermal administration.

According to one embodiment of the present invention, the effective amount of the azepine derivatives of Formula 1 or pharmaceutically acceptable salts thereof as a serotonin 5-$HT_7$ receptor modulator in the pharmaceutical composition is from 0.01 to 1000 mg/day for an adult patient. The dose of the azepine derivatives of Formula 1 or pharmaceutically acceptable salts thereof may be dependent on the age, body weight, sex, and general health of patients, the mode of administration, and the severity of diseases to be treated. The pharmaceutical compositions may be administered in single or divided doses per day according to the judgment of the physician or pharmacist.

Thus, the present invention provides the medical use of the azepine derivatives represented by Formula 1 or pharmaceutically acceptable salts thereof or the pharmaceutical compositions for preventing and treating diseases.

That is, the present invention includes the medical use of the azepine derivatives represented by Formula 1 or pharmaceutically acceptable salts thereof as 5-$HT_7$ receptor modulators or the pharmaceutical compositions for preventing and treating depression, migraine, anxiety, pain, particularly, neurological disorders such as inflammatory pain and neuropathic pain, body temperature dysregulation, biorhythm dysregulation, sleep disturbance, and smooth muscle diseases.

The present invention will be explained in more detail with reference to the following examples. However, it will be obvious to those skilled in the art that these examples are provided for illustrative purposes and are not intended to limit the scope of the invention.

EXAMPLES

Example 1

Step 1: Preparation of 1-(tert-butyl) 4-ethyl 5-oxoazepane-1,4-dicarboxylate tert-butyl 4-oxopiperidine-1-carboxylate (10 g, 50.1 mmol) was dissolved in diethyl ether (100 ml) in a reaction vessel, and then solutions of ethyl diazoacetate (6.85 ml, 65.1 mmol) in diethyl ether and $BF_3OEt_2$ (6.61 ml, 52.6 mmol) in diethyl ether were sequentially slowly added thereto at −20° C. The mixture was stirred at the same temperature for 1 h. After completion of the reaction, the temperature was allowed to rise to room temperature and 30% $K_2CO_3$ was added thereto until nitrogen gas was no longer evolved. Thereafter, the organic layer was separated, dried over anhydrous $Na_2SO_4$, and filtered. The filtrate was concentrated under reduced pressure to afford the desired compound. The product was used in the next reaction without further purification.

Step 2: Preparation of 1-(tert-butyl) 3-oxo-2,3,4,5,7,8-hexahydropyrazolo[3,4-d]azepine-6 (1H)-carboxylate 1-(tert-butyl) 4-ethyl 5-oxoazepane-1,4-dicarboxylate (14.3 g, 50.1 mmol) was dissolved in ethanol (100 ml) in a reaction vessel, and then hydrazine (35% in water, 7.6 ml, 85.2 mmol) was added thereto. The mixture was heated to reflux for 2 days. After completion of the reaction, the reaction mixture was allowed to cool to room temperature. Distilled water was added to the reaction mixture and the resulting solid was filtered to afford the desired compound (4.3 g, 16.98 mmol, 34% in 2 steps).

$^1$H NMR (300 MHz, DMSO) δ 3.44-3.39 (m, 4H), 2.65 (brs, 2H), 2.41 (brs, 2H), 1.41 (s, 9H)

Step 3: Preparation of di-tert-butyl 3-(((trifluoromethyl)sulfonyl)oxy)-4,5,7,8-hexahydropyrazolo[3,4-d]azepine-1,6-dicarboxylate Di-tert-butyl 3-oxo-2,3,4,5,7,8-hexahydropyrazolo[3,4-d]azepine-1,6-dicarboxylate (8.8 g, 24.90 mmol) was dissolved in dichloromethane (100 ml) in a reaction vessel, and then $Tf_2NPh$ (13.3 g, 37.35 mmol) and DIPEA (5.2 ml, 29.88 mmol) were added thereto. The mixture was heated to reflux for 12 h. After completion of the reaction, the reaction mixture was concentrated under reduced pressure and the resulting concentrate was purified by column chromatography (hexane:EA=10:1) to afford 11.24 g (23.15 mmol, 93%) of the desired compound.

$^1$H NMR (300 MHz, $CDCl_3$) δ 3.68-3.58 (m, 4H), 3.37 (brs, 2H), 2.71-2.70 (m, 2H), 1.62 (s, 9H), 1.48 (s, 9H)

Step 4: Preparation of 3-phenyl-1,4,5,6,7,8-hexahydropyrazolo[3,4-d]azepine

Di-tert-butyl 3-(((trifluoromethyl) sulfonyl)oxy)-4,5,7,8-hexahydropyrazolo[3,4-d]azepine-1,6-dicarboxylate (300 mg, 0.62 mmol), phenylboronic acid (113 mg, 0.93 mmol), $PdCl_2(dppf)$ (51 mg, 0.062 mmol), and $K_3PO_4$ (263 mg, 1.24 mmol) were dissolved in tetrahydrofuran (10 ml) in a reaction vessel. The solution was heated to reflux at 70° C. for 24 h. After completion of the reaction, the reaction mixture was filtered and the filtrate was concentrated under reduced pressure. The resulting concentrate was purified by column chromatography (hexane:EA=13:1) to give di-tert-butyl 3-phenyl-4,5,7,8-tetrahydropyrazolo[3,4-d]azepine-1,6-dicarboxylate (120 mg, 0.29 mmol, 47%). The intermediate was again dissolved in dichloromethane (5 ml) and 1 N HCl (in $Et_2O$, 2.66 ml, 2.66 mmol) was added thereto. The mixture was stirred for 12 h. After completion of the reaction, the reaction mixture was filtered. The filtered solid was dissolved in 1 N NaOH and extracted with dichloromethane. The obtained organic layer was dried over anhydrous $MgSO_4$ and filtered. The filtrate was concentrated under reduced pressure to afford 9 mg (0.042 mmol, 16%) of the desired compound.

$^1$H NMR (300 MHz, $CDCl_3$) δ 7.47-7.35 (m, 5H), 3.00-2.93 (m, 4H), 2.86-2.82 (m, 2H), 2.78-2.75 (m, 2H)

$^{13}$C NMR (75 MHz, $CDCl_3$) δ 149.75, 144.84, 131.85, 128.64, 128.12, 127.90, 116.79, 50.51, 48.69, 32.13, 28.12

Example 2

Preparation of 3-(2-fluorophenyl)-1,4,5,6,7,8-hexahydropyrazolo[3,4-d]azepine 6 mg (0.026 mmol, 28%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (300 mg, 0.62 mmol), 2-fluorophenylboronic acid (130 mg, 0.93 mmol), $PdCl_2$(dppf) (51 mg, 0.062 mmol), and $K_3PO_4$ (263 mg, 1.24 mmol) were used to obtain di-tert-butyl 3-(2-fluorophenyl)-4,5,7,8-tetrahydropyrazolo[3,4-d]azepine-1,6-dicarboxylate (40 mg, 0.093 mmol, 15%), which was then reacted with 1 N HCl (in $Et_2O$, 2 ml).

$^1$H NMR (300 MHz, $CDCl_3$) δ 7.43-7.31 (m, 2H), 7.21-7.11 (m, 2H), 3.02-2.93 (m, 4H), 2.87-2.84 (m, 2H), 2.67-2.63 (m, 2H)

$^{13}$C NMR (75 MHz, $CDCl_3$) δ 159.77 (d, J=246 Hz), 149.09, 139.44, 131.02 (d, J=3.7 Hz), 129.92 (d, J=8.2 Hz), 124.29 (d, J=3.0 Hz), 119.65 (d, J=15 Hz), 118.50, 116.05 (d, J=22.5 Hz), 50.32, 48.67, 32.12, 28.37

Example 3

Preparation of 3-(3-fluorophenyl)-1,4,5,6,7,8-hexahydropyrazolo[3,4-d]azepine 72 mg (0.31 mmol, 72%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (1 g, 2.06 mmol), 3-fluorophenylboronic acid (432 mg, 3.09 mmol), $PdCl_2$(dppf) (168 mg, 0.21 mmol), and $K_3PO_4$ (875 mg, 4.21 mmol) were used to obtain di-tert-butyl 3-(3-fluorophenyl)-4,5,7,8-tetrahydropyrazolo[3,4-d]azepine-1,6-dicarboxylate (350 mg, 0.81 mmol, 39%), which was then reacted with 1 N HCl (in $Et_2O$, 10 ml).

$^1$H NMR (300 MHz, $CDCl_3$) δ 7.42-7.15 (m, 3H), 7.05-6.99 (m, 1H), 2.98-2.92 (m, 4H), 2.79-2.70 (m, 4H)

$^{13}$C NMR (75 MHz, $CDCl_3$) δ 162.75 (d, J=224.5 Hz), 147.36, 145.70, 134.83 (d, J=7.5 Hz), 130.02 (d, J=8.25 Hz), 124.00 (d, J=2.25 Hz), 116.77, 115.14 (d, J=22.5 Hz), 114.49 (d, J=21 Hz), 50.33, 48.41, 31.19, 28.02

Example 4

Preparation of 3-(2-chlorophenyl)-1,4,5,6,7,8-hexahydropyrazolo[3,4-d]azepine 46 mg (0.19 mmol, 81%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (1 g, 2.06 mmol), 2-chlorophenylboronic acid (483 mg, 3.09 mmol), $PdCl_2$(dppf) (168 mg, 0.21 mmol), and $K_3PO_4$ (875 mg, 4.21 mmol) were used to obtain di-tert-butyl 3-(2-chlorophenyl)-4,5,7,8-tetrahydropyrazolo[3,4-d]azepine-1,6-dicarboxylate (105 mg, 0.23 mmol, 11%), which was then reacted with 1 N HCl (in $Et_2O$, 10 ml).

$^1$H NMR (300 MHz, $CDCl_3$) δ 7.45-7.42 (m, 1H), 7.36-7.24 (m, 3H), 2.94-2.90 (m, 4H), 2.69 (t, J=4.9 Hz, 2H), 2.51 (t, J=4.9 Hz, 2H)

$^{13}$C NMR (75 MHz, $CDCl_3$) δ 147.62, 143.42, 133.92, 132.12, 131.45, 129.76, 129.57, 126.61, 118.38, 50.13, 48.64, 31.57, 28.42

Example 5

Preparation of 3-(3-chlorophenyl)-1,4,5,6,7,8-hexahydropyrazolo[3,4-d]azepine 68 mg (0.27 mmol, 49%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (1 g, 2.06 mmol), 3-chlorophenylboronic acid (483 mg, 3.09 mmol), $PdCl_2$(dppf) (168 mg, 0.21 mmol), and $K_3PO_4$ (875 mg, 4.21 mmol) were used to obtain di-tert-butyl 3-(3-chlorophenyl)-4,5,7,8-tetrahydropyrazolo[3,4-d]azepine-1,6-dicarboxylate (305 mg, 0.68 mmol, 33%) and 250 mg (0.56 mmol) of the intermediate was then reacted with 1 N HCl (in $Et_2O$, 15 ml).

$^1$H NMR (300 MHz, $CDCl_3$) δ 7.43 (s, 1H), 7.32-7.27 (m, 3H), 2.95-2.90 (m, 4H), 2.74-2.68 (m, 4H)

$^{13}$C NMR (75 MHz, $CDCl_3$) δ 147.35, 145.62, 134.53, 134.37, 129.72, 128.26, 127.68, 126.45, 116.87, 50.39, 48.50, 31.32, 28.14

Example 6

Preparation of 3-(4-chlorophenyl)-1,4,5,6,7,8-hexahydropyrazolo[3,4-d]azepine 45 mg (0.18 mmol, 73%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (590 mg, 1.22 mmol), 4-chlorophenylboronic acid (228 mg, 1.46 mmol), $PdCl_2$(dppf) (498 mg, 0.61 mmol), and $K_3PO_4$ (518 mg, 2.44 mmol) were used to obtain di-tert-butyl 3-(3-chlorophenyl)-4,5,7,8-tetrahydropyrazolo[3,4-d]azepine-1,6-dicarboxylate (110 mg, 0.25 mmol, 20%), which was then reacted with 1 N HCl (in $Et_2O$, 10 ml).

$^1$H NMR (300 MHz, $CDCl_3$) δ 7.41-7.30 (m, 4H), 2.99-2.94 (m, 4H), 2.80-2.71 (m, 4H)

$^{13}$C NMR (75 MHz, $CDCl_3$) δ 147.88, 145.42, 133.77, 130.88, 129.47, 128.72, 116.81, 50.45, 48.56, 31.55, 28.14

Example 7

Preparation of 3-(o-tolyl)-1,4,5,6,7,8-hexahydropyrazolo[3,4-d]azepine 62 mg (0.27 mmol, 55%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (1 g, 2.06 mmol), 2-methylphenylboronic acid (420 mg, 3.09 mmol), $PdCl_2$(dppf) (168 mg, 0.21 mmol), and $K_3PO_4$ (875 mg, 4.21 mmol) were used to obtain di-tert-butyl 3-(o-tolyl)-4,5,7,8-tetrahydropyrazolo[3,4-d]azepine-1,6-dicarboxylate (215 mg, 0.50 mmol, 24%), which was then reacted with 1 N HCl (in $Et_2O$, 15 ml).

$^1$H NMR (300 MHz, $CDCl_3$) δ 7.26-7.17 (m, 4H), 2.83 (q, J=4.9 Hz, 4H), 2.53 (t, J=4.7 Hz, 2H), 2.41 (t, J=4.6 Hz, 2H), 2.17 (s, 3H)

$^{13}$C NMR (75 MHz, $CDCl_3$) δ 149.32, 143.75, 137.51, 131.35, 130.58, 130.12, 128.41, 125.50, 117.53, 50.40, 48.86, 31.83, 28.10, 19.87

Example 8

Preparation of 3-(m-tolyl)-1,4,5,6,7,8-hexahydropyrazolo[3,4-d]azepine 21 mg (0.092 mmol, 33%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (1 g, 2.06 mmol), 3-methylphenylboronic acid (420 mg, 3.09 mmol), PdCl$_2$(dppf) (168 mg, 0.21 mmol), and K$_3$PO$_4$ (875 mg, 4.21 mmol) were used to obtain di-tert-butyl 3-(m-tolyl)-4,5,7,8-tetrahydropyrazolo[3,4-d]azepine-1,6-dicarboxylate (120 mg, 0.28 mmol, 14%), which was then reacted with 1 N HCl (in Et$_2$O, 10 ml).

$^1$H NMR (300 MHz, CDCl$_3$) δ 7.35-7.30 (m, 1H), 7.26-7.17 (m, 3H), 3.05-3.02 (m, 2H), 2.98-2.90 (m, 4H), 2.79-2.76 (m, 2H), 2.40 (s, 3H)

$^{13}$C NMR (75 MHz, CDCl$_3$) δ 149.30, 144.43, 138.46, 131.29, 128.87, 128.69, 128.63, 125.18, 116.09, 49.81, 48.00, 30.61, 26.60, 21.45

Example 9

Preparation of 3-(p-tolyl)-1,4,5,6,7,8-hexahydropyrazolo[3,4-d]azepine 125 mg (0.55 mmol, 58%) of the desired compound was prepared in the same manner as in Example 1, except that di-tert-butyl 3-(((trifluoromethyl)sulfonyl)oxy)-4,5,7,8-hexahydropyrazolo[3,4-d]azepine-1,6-dicarboxylate (1 g, 2.06 mmol), 4-methylphenylboronic acid (420 mg, 3.09 mmol), PdCl$_2$(dppf) (168 mg, 0.21 mmol), and K$_3$PO$_4$ (875 mg, 4.21 mmol) were used to obtain di-tert-butyl 3-(p-tolyl)-4,5,7,8-tetrahydropyrazolo[3,4-d]azepine-1,6-dicarboxylate (405 mg, 0.95 mmol, 46%), which was then reacted with 1 N HCl (in Et$_2$O, 15 ml).

$^1$H NMR (300 MHz, CDCl$_3$) δ 7.51 (brs, 1H), 7.29 (d, J=7.8 Hz, 2H), 7.12 (d, J=7.5 Hz, 2H), 2.87 (brs, 4H), 2.71-2.69 (m, 4H), 2.32 (s, 3H)

$^{13}$C NMR (75 MHz, CDCl$_3$) δ 148.81, 145.19, 137.36, 129.37, 129.16, 128.22, 116.30, 50.44, 48.58, 31.77, 28.16, 21.26

Example 10

Preparation of 3-phenyl-5,6,7,8-tetrahydro-4H-isoxazolo[4,5-d]azepine 9 mg (0.042 mmol, 28%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (100 mg, 0.28 mmol), phenylboronic acid (41 mg, 0.33 mmol), Pd(PPh$_3$)$_4$ (26 mg, 0.022 mmol), K$_3$PO$_4$ (178 mg, 0.84 mmol), and KBr (37 mg, 0.31 mmol) were used to obtain ethyl 3-phenyl-4,5,7,8-tetrahydro-6H-isoxazolo[3,4-d]azepine-6-carboxylate (15 mg, 0.052 mmol, 19%), which was then reacted with HBr (33% in AcOH, 0.450 ml).

$^1$H NMR (300 MHz, CDCl$_3$) δ 7.62-7.35 (m, 5H), 3.03 (brs, 4H), 2.91-2.88 (m, 2H), 2.77-2.74 (m, 2H)

$^{13}$C NMR (75 MHz, CDCl$_3$) δ 161.89, 141.20, 128.95, 128.55, 127.12, 120.46, 112.11, 47.05, 46.58, 40.50, 36.0

Example 11

Preparation of 3-(2-fluorophenyl)-5,6,7,8-tetrahydro-4H-isoxazolo[4,5-d]azepine 24 mg (0.10 mmol, 79%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 2-fluorophenylboronic acid (187 mg, 1.34 mmol), PdCl$_2$(dppf) (91 mg, 0.11 mmol), K$_3$PO$_4$ (713 mg, 3.36 mmol), and KBr (147 mg, 1.23 mmol) were used to obtain ethyl 3-(2-fluorophenyl)-4,5,7,8-tetrahydro-6H-isoxazolo[3,4-d]azepine-6-carboxylate (78 mg, 0.26 mmol, 23%) and 40 mg (0.13 mmol) of the intermediate was then reacted with HBr (33% in AcOH, 0.450 ml).

$^1$H NMR (300 MHz, CDCl$_3$) δ 7.38-7.30 (m, 2H), 7.22-7.10 (m, 2H), 3.18-2.97 (m, 4H), 2.85-2.70 (m 4H)

$^{13}$C NMR (75 MHz, CDCl$_3$) δ 159.00 (d, J=236.25 Hz), 130.72 (d, J=8.25 Hz), 129.57, 129.53, 129.26 (d, J=14.25 Hz), 124.29 (d, J=3 Hz), 119.61, 116.05 (d, J=21 Hz), 115.25, 47.04, 46.38, 40.40, 36.18

Example 12

Preparation of 3-(3-fluorophenyl)-5,6,7,8-tetrahydro-4H-isoxazolo[4,5-d]azepine 44 mg (0.19 mmol, 95%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 3-fluorophenylboronic acid (187 mg, 1.34 mmol), PdCl$_2$(dppf) (91 mg, 0.11 mmol), K$_3$PO$_4$ (713 mg, 3.36 mmol), and KBr (147 mg, 1.23 mmol) were used to obtain ethyl 3-(3-fluorophenyl)-4,5,7,8-tetrahydro-6H-isoxazolo[3,4-d]azepine-6-carboxylate (98 mg, 0.32 mmol, 29%) and 60 mg (0.20 mmol) of the intermediate was then reacted with of and HBr (33% in AcOH, 0.450 ml).

$^1$H NMR (400 MHz, CDCl$_3$) δ 7.38-7.06 (m, 4H), 2.99 (brs, 4H), 2.83 (brs, 2H), 2.72 (brs, 2H)

$^{13}$C NMR (100 MHz, CDCl$_3$) δ 162.51 (d, J=245 Hz), 160.48, 143.30 (d, J=7 Hz), 130.22 (d, J=8 Hz), 122.97 (d, J=3 Hz), 120.01, 115.78 (d, J=21 Hz), 114.19 (d, J=22 Hz), 113.15, 47.02, 46.59, 40.54, 36.19

Example 13

Preparation of 3-(4-fluorophenyl)-5,6,7,8-tetrahydro-4H-isoxazolo[4,5-d]azepine 42 mg (0.18 mmol, 50%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 4-fluorophenylboronic acid (187 mg, 1.34 mmol), PdCl$_2$(dppf) (91 mg, 0.11 mmol), K$_3$PO$_4$ (713 mg, 3.36 mmol), and KBr (147 mg, 1.23 mmol) were used to obtain ethyl 3-(4-fluorophenyl)-4,5,7,8-tetrahydro-6H-isoxazolo[3,4-d]azepine-6-carboxylate (112 mg, 0.37 mmol, 33%), which was then reacted with HBr (33% in AcOH, 0.750 ml).

$^1$H NMR (300 MHz, CDCl$_3$) δ 7.41-7.36 (m, 2H), 7.13-7.07 (m, 2H), 3.09-2.92 (m, 4H), 2.90-2.80 (m, 2H), 2.79-2.69 (m, 2H)

¹³C NMR (75 MHz, CDCl₃) δ 162.85 (d, J=247.5 Hz), 160.86, 137.26 (d, J=3.75 Hz), 129.15 (d, J=8.25 Hz), 120.35, 115.58 (d, J=11.25 Hz), 112.40, 47.06, 46.58, 40.40, 36.11

Example 14

Preparation of 3-(2-chlorophenyl)-5,6,7,8-tetrahydro-4H-isoxazolo[4,5-d]azepine 6 mg (0.024 mmol, 16%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (200 mg, 0.56 mmol), 2-chlorophenylboronic acid (104 mg, 0.66 mmol), Pd(PPh₃)₄ (52 mg, 0.044 mmol), K₃PO₄ (356 mg, 1.68 mmol), and KBr (74 mg, 0.62 mmol) were used to obtain ethyl 3-(2-chlorophenyl)-4,5,7,8-tetrahydro-6H-isoxazolo[3,4-d]azepine-6-carboxylate (48 mg, 0.15 mmol, 27%), which was then reacted with HBr (33% in AcOH, 0.750 ml).

¹H NMR (300 MHz, CDCl₃) δ 7.45-7.40 (m, 1H), 7.33-7.23 (m, 3H), 3.10-2.90 (m, 4H), 2.80-2.65 (m, 4H)

¹³C NMR (75 MHz, CDCl₃) δ 160.38, 140.77, 131.41, 130.00, 129.84, 129.32, 127.14, 119.30, 115.34, 47.27, 46.77, 40.27, 36.03

Example 15

Preparation of 3-(3-chlorophenyl)-5,6,7,8-tetrahydro-4H-isoxazolo[4,5-d]azepine 16 mg (0.056 mmol, 86%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (100 mg, 0.28 mmol), 3-chlorophenylboronic acid (52 mg, 0.33 mmol), Pd(PPh₃)₄ (26 mg, 0.022 mmol), K₃PO₄ (178 mg, 0.84 mmol), and KBr (37 mg, 0.31 mmol) were used to obtain ethyl 3-(3-chlorophenyl)-4,5,7,8-tetrahydro-6H-isoxazolo[3,4-d]azepine-6-carboxylate (25 mg, 0.078 mmol, 28%), which was then reacted with HBr (33% in AcOH, 0.300 ml).

¹H NMR (300 MHz, CDCl₃) δ 7.45-7.25 (m, 4H), 3.12-2.95 (m, 4H), 2.87-2.80 (m, 2H), 2.79-2.71 (m, 2H)

¹³C NMR (75 MHz, CDCl₃) δ 160.27, 143.02, 134.49, 129.89, 128.94, 127.15, 125.42, 119.90, 113.39, 47.08, 46.64, 40.53, 36.21

Example 16

Preparation of 3-(4-chlorophenyl)-5,6,7,8-tetrahydro-4H-isoxazolo[4,5-d]azepine 21 mg (0.084 mmol, 70%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (115 mg, 0.32 mmol), 4-chlorophenylboronic acid (75 mg, 0.48 mmol), PdCl₂(dppf) (26 mg, 0.032 mmol), and K₃PO₄ (136 mg, 0.64 mmol) were used to obtain ethyl 3-(4-chlorophenyl)-4,5,7,8-tetrahydro-6H-isoxazolo[3,4-d]azepine-6-carboxylate (38 mg, 0.12 mmol, 37%), which was then reacted with HBr (33% in AcOH, 0.450 ml).

¹H NMR (400 MHz, CDCl₃) δ 7.39 (dd, J=6.6, 2.0 Hz, 2H), 7.35-7.29 (m, 2H), 3.01-2.99 (m, 4H), 2.85-2.82 (m, 2H), 2.73-2.71 (m, 2H)

¹³C NMR (100 MHz, CDCl₃) δ 160.64, 139.59, 134.87, 128.78, 128.56, 120.19, 112.77, 47.02, 46.57, 40.51, 36.13

Example 17

Preparation of 3-(o-tolyl)-5,6,7,8-tetrahydro-4H-isoxazolo[4,5-d]azepine 42 mg (0.18 mmol, 61%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 2-methylphenylboronic acid (182 mg, 1.34 mmol), PdCl₂(dppf) (91 mg, 0.11 mmol), K₃PO₄ (713 mg, 3.36 mmol), and KBr (147 mg, 1.23 mmol) were used to obtain ethyl 3-(o-tolyl)-4,5,7,8-tetrahydro-6H-isoxazolo[3,4-d]azepine-6-carboxylate (64 mg, 0.22 mmol, 19%) and 90 mg (0.30 mmol) of the intermediate was then reacted with HBr (33% in AcOH, 0.900 ml).

¹H NMR (400 MHz, CDCl₃) δ 7.29-7.21 (m, 3H), 7.12 (d, J=6.8 Hz, 1H), 3.04-2.95 (m, 4H), 2.80-2.62 (m, 4H), 2.31 (s, 3H)

¹³C NMR (100 MHz, CDCl₃) δ 162.98, 141.96, 133.76, 130.58, 128.42, 127.15, 126.15, 119.72, 114.07, 47.61, 46.77, 40.75, 35.80, 19.78

Example 18

Preparation of 3-(m-tolyl)-5,6,7,8-tetrahydro-4H-isoxazolo[4,5-d]azepine 21 mg (0.092 mmol, 44%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 3-methylphenylboronic acid (182 mg, 1.34 mmol), PdCl₂(dppf) (91 mg, 0.11 mmol), K₃PO₄ (713 mg, 3.36 mmol), and KBr (147 mg, 1.23 mmol) were used to obtain ethyl 3-(m-tolyl)-4,5,7,8-tetrahydro-6H-isoxazolo[3,4-d]azepine-6-carboxylate (64 mg, 0.22 mmol, 19%), which was then reacted with HBr (33% in AcOH, 0.600 ml).

¹H NMR (400 MHz, CDCl₃) δ 7.33-7.29 (m, 1H), 7.23-7.17 (m, 3H), 3.04-3.00 (m, 4H), 2.91-2.83 (m, 2H), 2.76-2.71 (m, 2H), 2.40 (s, 3H)

¹³C NMR (100 MHz, CDCl₃) δ 162.00, 141.14, 138.21, 129.69, 128.43, 127.66, 124.20, 120.43, 111.79, 46.91, 46.42, 40.21, 35.77, 21.40

Example 19

Preparation of 3-(p-tolyl)-5,6,7,8-tetrahydro-4H-isoxazolo[4,5-d]azepine 20 mg (0.088 mmol, 44%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 4-methylphenylboronic acid (182 mg, 1.34 mmol), PdCl₂(dppf) (91 mg, 0.11 mmol), K₃PO₄ (713 mg, 3.36 mmol), and KBr (147 mg, 1.23 mmol) were used to obtain ethyl 3-(p-tolyl)-4,5,7,8-tetrahydro-6H-isoxazolo[3,4-d]azepine-6-carboxylate (85 mg, 0.28 mmol, 25%) and 60 mg (0.20 mmol) of the intermediate was then reacted with HBr (33% in AcOH, 0.600 ml).

¹H NMR (300 MHz, CDCl₃) δ 7.32 (d, J=8.1 Hz, 2H), 7.23 (d, J=8.1 Hz, 2H), 3.03-2.99 (m, 4H), 2.88-2.85 (m, 2H), 2.75-2.70 (m, 2H), 2.40 (s, 3H)

$^{13}$C NMR (75 MHz, CDCl$_3$) δ 161.96, 139.02, 138.33, 129.18, 127.10, 120.76, 111.47, 47.13, 46.64, 40.67, 36.21, 21.30

Example 20

Preparation of 3-(2-methoxyphenyl)-5,6,7,8-tetrahydro-4H-isoxazolo[4,5-d]azepine 13 mg (0.053 mmol, 44%) of the desired compound was prepared in the same manner as in Example 1, except that ethyl 3-(((trifluoromethyl)sulfonyl)oxy)-4,5,7,8-tetrahydro-6H-isoxazolo[4,5-d]azepine-6-carboxylate (400 mg, 1.12 mmol), 2-methoxyphenylboronic acid (204 mg, 1.34 mmol), PdCl$_2$(dppf) (91 mg, 0.11 mmol), K$_3$PO$_4$ (713 mg, 3.36 mmol), and KBr (147 mg, 1.23 mmol) were used to obtain ethyl 3-(2-methoxyphenyl)-4,5,7,8-tetrahydro-6H-isoxazolo[3,4-d]azepine-6-carboxylate (40 mg, 0.13 mmol, 11%), which was then reacted with HBr (33% in AcOH, 0.450 ml).

$^1$H NMR (300 MHz, CDCl$_3$) δ 7.39-7.33 (m, 1H), 7.26 (dd, J=7.5, 1.8 Hz, 1H), 7.03-6.93 (m, 2H), 3.87 (s, 3H), 3.03-3.00 (m, 4H), 2.74-2.70 (m, 4H)

$^{13}$C NMR (75 MHz, CDCl$_3$) δ 161.38, 156.01, 130.73, 130.18, 129.13, 120.63, 120.23, 113.30, 111.01, 55.40, 47.10, 46.46, 40.41, 36.11

Formulation Example 1

Formulation of the Azepine Compounds

The azepine derivatives synthesized in Examples 1-20 were prepared into various formulations.

Formulation Example 1.1

5.0 mg of each of the azepine derivatives synthesized in Examples 1-20 as an active ingredient was sieved and mixed with 14.1 mg of lactose, 0.8 mg of crospovidone USNF, and 0.1 mg of magnesium stearate. The mixture was compressed to produce tablets.

Formulation Example 1.2

Tableting by Wet Granulation 5.0 mg of each of the azepine derivatives synthesized in Examples 1-20 as an active ingredient was sieved and mixed with 16.0 mg of lactose and 4.0 mg of starch. To the mixture was added an appropriate amount of a solution of polysorbate 80 (0.3 mg) in pure water. The resulting mixture was atomized, dried, sieved, mixed with 2.7 mg of colloidal silicon dioxide and 2.0 mg of magnesium stearate, and compressed to produce tablets.

Formulation Example 1.3

Powders and Capsules 5.0 mg of each of the azepine derivatives synthesized in Examples 1-20 as an active ingredient was sieved, mixed with 14.8 mg of lactose, 10.0 mg of polyvinyl pyrrolidone, and 0.2 mg of magnesium stearate, and filled in hard No. 5 gelatin capsules.

Formulation Example 1.4

Injectables 100 mg of each of the azepine derivatives synthesized in Examples 1-20 as an active ingredient, 180 mg of mannitol as an excipient, 26 mg of Na$_2$HPO$_4$.12H$_2$O, and 2974 mg of distilled water were mixed together to produce an injectable.

Test Example 1

Measurement of Binding Affinity for Serotonin 5-HT$_7$ Receptor

Human gene recombinant 5-HT$_7$ receptor expressed in Chinese hamster ovary (CHO) cells was used. [$^3$H]LSD 1 nM, the 5-HT$_7$ receptor membrane (15 μg/well), each of the samples of Example 1-20 at various concentrations, 10 mM MgCl$_2$, and 50 mM Tris-HCl buffer (pH 7.4) containing 0.1 mM EDTA were added to a vessel until the final volume reached 0.25 ml. The reaction mixture was incubated at 25° C. for 90 min. The incubated reaction mixture was rapidly passed through a Whatman GF/C glass fiber filter, which had been previously soaked with 0.3% polyethyleneimine, using a Brandel-Harvester to quench the reaction and washed with cold 50 mM Tris-HCl buffer. The filter was covered with MeltiLex, sealed in a sample bag, and dried in an oven. The radioactivity retained in the filter was counted using Micro-Beta (Wallac). Non-specific binding was determined in the presence of 0.5 μM Mianserin. The K$_i$ value of the test drug was calculated from a nonlinear regression (GraphPad Prism Program, San Diego, USA) of the isotherm curves obtained from 2 repeated tests for two test tubes with concentrations of 10th and 11th steps test.

The % inhibition and binding affinity (K$_i$) values of the novel compounds (10 mM each) for the serotonin 5-HT$_7$ receptor are shown in Table 1.

TABLE 1

| Test compound | % inhibition (10 μM) | K$_i$ (nM) |
|---|---|---|
| Example 1 | 84.2 | 322 |
| Example 2 | 78.9 | 714 |
| Example 3 | 72.9 | 1243 |
| Example 4 | 88.7 | 386 |
| Example 5 | 79.2 | 883 |
| Example 6 | 96.4 | 30 |
| Example 7 | 68.5 | 881 |
| Example 8 | 63.0 | 1436 |
| Example 9 | 94.2 | 47 |
| Example 10 | 84.3 | 319 |
| Example 11 | 77.9 | 366 |
| Example 12 | 57.5 | 1407 |
| Example 13 | 94.6 | 53 |
| Example 14 | 84.5 | 425 |
| Example 15 | 78.7 | 369 |
| Example 16 | 93.8 | 70 |
| Example 17 | 41.8 | — |
| Example 18 | 76.3 | 506 |
| Example 19 | 96.3 | 16 |
| Example 20 | 87.9 | 303 |

As shown in Table 1, the azepine derivatives of Examples 1-30 were found to have high inhibitory activities on and high binding affinities for the 5-HT$_7$ receptor. Particularly, the azepine derivatives having a substituent at the 4-position of the aryl ring exerted considerably improved inhibitory activities on and binding affinities for the 5-HT$_7$ receptor. The azepine derivatives having a pyrazoloazepine structure showed somewhat better inhibitory effects than the azepine derivatives having a pyrazoloazepine structure.

What is claimed is:
1. Azepine derivatives acting on a 5-HTS receptor, the azepine derivative selected from the group consisting of:

Compound 2: 3-(2-Fluorophenyl)-1,4,5,6,7,8-hexahydropyrazolo[3,4-d]azepine;

Compound 3: 3-(3-Fluorophenyl)-1,4,5,6,7,8-hexahydropyrazolo[3,4-d]azepine;

Compound 4: 3-(2-Chlorophenyl)-1,4,5,6,7,8-hexahydropyrazolo[3,4-d]azepine;

Compound 5: 3-(3-Chlorophenyl)-1,4,5,6,7,8-hexahydropyrazolo[3,4-d]azepine;

Compound 7: 3-(o-tolyl)-1,4,5,6,7,8-hexahydropyrazolo[3,4-d]azepine;

Compound 8: 3-(m-tolyl)-1,4,5,6,7,8-hexahydropyrazolo[3,4-d]azepine;

Compound 9: 3-(p-tolyl)-1,4,5,6,7,8-hexahydropyrazolo[3,4-d]azepine;

Compound 10: 3-Phenyl-5,6,7,8-tetrahydro-4H-isoxazolo[4,5-d]azepine;

Compound 11: 3-(2-Fluorophenyl)-5,6,7,8-tetrahydro-4H-isoxazolo[4,5-d]azepine;

Compound 12: 3-(3-fluorophenyl)-5,6,7,8-tetrahydro-4H-isoxazolo[4,5-d]azepine;

Compound 13: 3-(4-Fluorophenyl)-5,6,7,8-tetrahydro-4H-isoxazolo[4,5-d]azepine;

Compound 14: 3-(2-Chlorophenyl)-5,6,7,8-tetrahydro-4H-isoxazolo[4,5-d]azepine;

Compound 15: 3-(3-Chlorophenyl)-5,6,7,8-tetrahydro-4H-isoxazolo[4,5-d]azepine;

Compound 16: 3-(4-Chlorophenyl)-5,6,7,8-tetrahydro-4H-isoxazolo[4,5-d]azepine;

Compound 17: 3-(o-tolyl)-5,6,7,8-tetrahydro-4H-isoxazolo[4,5-d]azepine;

Compound 18: 3-(m-tolyl)-5,6,7,8-tetrahydro-4H-isoxazolo[4,5-d]azepine;

Compound 19: 3-(p-tolyl)-5,6,7,8-tetrahydro-4H-isoxazolo[4,5-d]azepine; and

Compound 20: 3-(2-Methoxyphenyl)-5,6,7,8-tetrahydro-4H-isoxazolo[4,5-d]azepine, or a pharmaceutically acceptable salt thereof.

2. The azepine derivatives or pharmaceutically acceptable salts thereof according to claim 1, wherein the pharmaceutically acceptable salt is a salt with an inorganic or organic acid selected from hydrochloric acid, hydrobromic acid, sulfonic acid, amidosulfuric acid, phosphoric acid, nitric acid, acetic acid, propionic acid, succinic acid, glycolic acid, stearic acid, lactic acid, tartaric acid, citric acid, para-toluenesulfonic acid, and methanesulfonic acid.

3. A method for preparing the azepine derivatives represented by Formula 1:

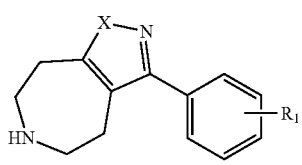
(1)

wherein X is NH or O and $R_1$ is selected from hydrogen, halogen, $C_1$-$C_6$ alkyl, $C_1$-$C_6$ alkoxy, halogenated $C_1$-$C_6$ alkyl, and hydroxyl, the method comprising subjecting a compound of Formula 2:

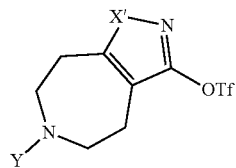
(2)

wherein X' is $NR_2$ or O, $R_2$ is —C(O)OC(CH$_3$)$_3$, Y is —C(O)OC(CH$_3$)$_3$ or —C(O)OCH$_2$CH$_3$ as an amine protecting group, and Tf is trifluoromethanesulfonyl, to the Suzuki coupling reaction with a compound of Formula 3:

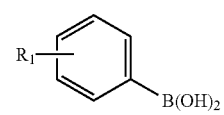
(3)

wherein $R_1$ is as defined in Formula 1, and removing the amine protecting group.

4. The method according to claim 3, wherein the compound of Formula 2 is prepared by reacting a compound of Formula 4:

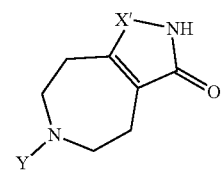
(4)

wherein X' is $NR_2$ or O, $R_2$ is —C(O)OC(CH$_3$)$_3$, Y is —C(O)OC(CH$_3$)$_3$ or —C(O)OCH$_2$CH$_3$ as an amine protecting group, Tf is trifluoromethanesulfonyl, and Ph is phenyl, with Tf$_2$NPh.

5. The method according to claim 4, wherein the compound of Formula 4 is prepared by a) reacting a compound of Formula 5:

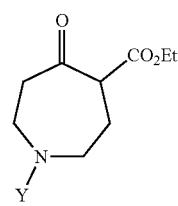
(5)

wherein Y is —C(O)OC(CH$_3$)$_3$ or —C(O)OCH$_2$CH$_3$ and Et is ethyl, with hydrazine and introducing $R_2$ ($R_2$ =—C(O)OC(CH$_3$)$_3$) into the compound of Formula 4, or b) reacting the compound of Formula 5 with ethylene glycol to protect the ketone group and reacting the reaction product with hydroxylamine, provided that when the compound of Formula 4 is prepared by a), Y in Formula 5 is —C(O)OC(CH$_3$)$_3$ and when the compound of Formula 4 is prepared by b), Y in Formula 5 is —C(O)OCH$_2$CH$_3$.

6. The method according to claim 5, wherein the compound represented by Formula 5 is prepared by reacting a compound represented by Formula 6:

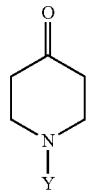
(6)

wherein Y is —C(O)OC(CH$_3$)$_3$ or —C(O)OCH$_2$CH$_3$, with ethyl diazoacetate and BF$_3$OEt.

7. A method of treating depression and anxiety in a subject in need thereof, comprising:
providing a pharmaceutical composition comprising, as active ingredient, a therapeutically effective amount of azepine derivative selected from the group consisting of:
Compound 1: 3-Phenyl-1,4,5,6,7,8-hexahydropyrazolo[3,4-d]azepine;
Compound 2: 3-(2-Fluorophenyl)-1,4,5,6,7,8-hexahydropyrazolo[3,4-d]azepine;
Compound 3: 3-(3-Fluorophenyl)-1,4,5,6,7,8-hexahydropyrazolo[3,4-d]azepine;
Compound 4: 3-(2-Chlorophenyl)-1,4,5,6,7,8-hexahydropyrazolo[3,4-d]azepine;
Compound 5: 3-(3-Chlorophenyl)-1,4,5,6,7,8-hexahydropyrazolo[3,4-d]azepine;
Compound 6: 3-(4-Chlorophenyl)-1,4,5,6,7,8-hexahydropyrazolo[3,4-d]azepine;
Compound 7: 3-(o-tolyl)-1,4,5,6,7,8-hexahydropyrazolo[3,4-d]azepine;
Compound 8: 3-(m-tolyl)-1,4,5,6,7,8-hexahydropyrazolo[3,4-d]azepine;
Compound 9: 3-(p-tolyl)-1,4,5,6,7,8-hexahydropyrazolo[3,4-d]azepine;
Compound 10: 3-Phenyl-5,6,7,8-tetrahydro-4H-isoxazolo[4,5-d]azepine;
Compound 11: 3-(2-Fluorophenyl)-5,6,7,8-tetrahydro-4H-isoxazolo[4,5-d]azepine;
Compound 12: 3-(3-fluorophenyl)-5,6,7,8-tetrahydro-4H-isoxazolo[4,5-]azepine;
Compound 13: 3-(4-Fluorophenyl)-5,6,7,8-tetrahydro-4H-isoxazolo[4,5-d]azepine;
Compound 14: 3-(2-Chlorophenyl)-5,6,7,8-tetrahydro-4H-isoxazolo[4,5-d]azepine;
Compound 15: 3-(3-Chlorophenyl)-5,6,7,8-tetrahydro-4H-isoxazolo[4,5-d]azepine;
Compound 16: 3-(4-Chlorophenyl)-5,6,7,8-tetrahydro-4H-isoxazolo[4,5-d]azepine;
Compound 17: 3-(o-tolyl)-5,6,7,8-tetrahydro-4H-isoxazolo[4,5-d]azepine;
Compound 18: 3-(m-tolyl)-5,6,7,8-tetrahydro-4H-isoxazolo[4,5-d]azepine;
Compound 19: 3-(p-tolyl)-5,6,7,8-tetrahydro-4H-isoxazolo[4,5-d]azepine; and
Compound 20: 3-(2-Methoxyphenyl)-5,6,7,8-tetrahydro-4H-isoxazolo[4,5-d]azepine, or a pharmaceutically acceptable salt thereof; and
administering the pharmaceutical composition to a subject, wherein the depression and anxiety is treated.

* * * * *